United States Patent
Olmsted

(10) Patent No.: US 9,559,492 B2
(45) Date of Patent: Jan. 31, 2017

(54) LASER SYSTEM WITH REDUCED APPARENT SPECKLE

(71) Applicant: LaserMax, Inc, Rochester, NY (US)

(72) Inventor: Brian L. Olmsted, Spencerport, NY (US)

(73) Assignee: LaserMax, Inc., Rochester, NY (US)

( * ) Notice: Subject to any disclaimer, the term of this patent is extended or adjusted under 35 U.S.C. 154(b) by 0 days.

(21) Appl. No.: 14/601,782

(22) Filed: Jan. 21, 2015

(65) Prior Publication Data

US 2016/0211647 A1 Jul. 21, 2016

Related U.S. Application Data

(60) Provisional application No. 61/929,762, filed on Jan. 21, 2014.

(51) Int. Cl.
| | |
|---|---|
| *H01S 3/00* | (2006.01) |
| *H01S 5/042* | (2006.01) |
| *G01N 21/88* | (2006.01) |
| *G02B 27/20* | (2006.01) |
| *G01N 21/956* | (2006.01) |
| *G02B 21/36* | (2006.01) |
| *G01N 21/47* | (2006.01) |
| *G02B 27/48* | (2006.01) |
| *H01S 5/022* | (2006.01) |

(52) U.S. Cl.
CPC ......... *H01S 5/0427* (2013.01); *G01N 21/8851* (2013.01); *G01N 21/956* (2013.01); *G01N 2021/479* (2013.01); *G01N 2201/06113* (2013.01); *G02B 21/365* (2013.01); *G02B 27/20* (2013.01); *G02B 27/48* (2013.01); *H01S 5/02288* (2013.01); *Y10S 378/901* (2013.01)

(58) Field of Classification Search
CPC ........ H01S 5/22; H01S 3/109; H01S 5/34333; H01S 5/0071; H01S 5/0655; H01S 5/141; H01S 3/0092; H01S 3/0627; H01S 3/08072; H01S 3/09415; H01S 3/2383; H01S 5/0202; H01S 5/4012; H01S 5/423
USPC ...................................... 372/38.02
See application file for complete search history.

(56) References Cited

U.S. PATENT DOCUMENTS

| | | | |
|---|---|---|---|
| 8,743,923 B2 | 6/2014 | Geske et al. | |
| 2011/0043768 A1* | 2/2011 | Nakayama | G02B 27/48 353/38 |
| 2012/0287958 A1* | 11/2012 | Lell | H01S 5/4043 372/45.01 |

OTHER PUBLICATIONS

Valle, "Experimental study of transverse mode dynamics in vertical-cavity surface-emitting lasers under current modulation", Proc. of SPIE vol. 6997, 69970Z, 2008.*

Saloma, et al. "Speckle reduction by wavelength and space diversity using a semiconductor laser", Applied Optics, vol. 29, No. 6 (OSA) 1990.

(Continued)

*Primary Examiner* — Xinning Niu
*Assistant Examiner* — Vu A Vu
(74) *Attorney, Agent, or Firm* — Roland R. Schindler, II; Dominic Ciminello; Lee & Hayes

(57) ABSTRACT

Laser systems with reduced apparent speckle are provided. The laser systems emit laser light having different mode structures that change within a time period of an integration period of an imaging system used to observe a field of view that is at least in part illuminated by the laser systems.

12 Claims, 10 Drawing Sheets

(56) References Cited

OTHER PUBLICATIONS

Valle, A. et al. "Experimental study of transverse mode dynamics in vertical-cavity surface-emitting lasers under aurrent modulation", Proc. of SPIE, vol. 6997, 69970Z, 2008.
Trisnadi, "Speckle contrast reduction in laser projection displays", Projection Displays VIII, Ming H. Wu, Editor proceedings of SPIE vol. 4657, SPIE 2002.

* cited by examiner

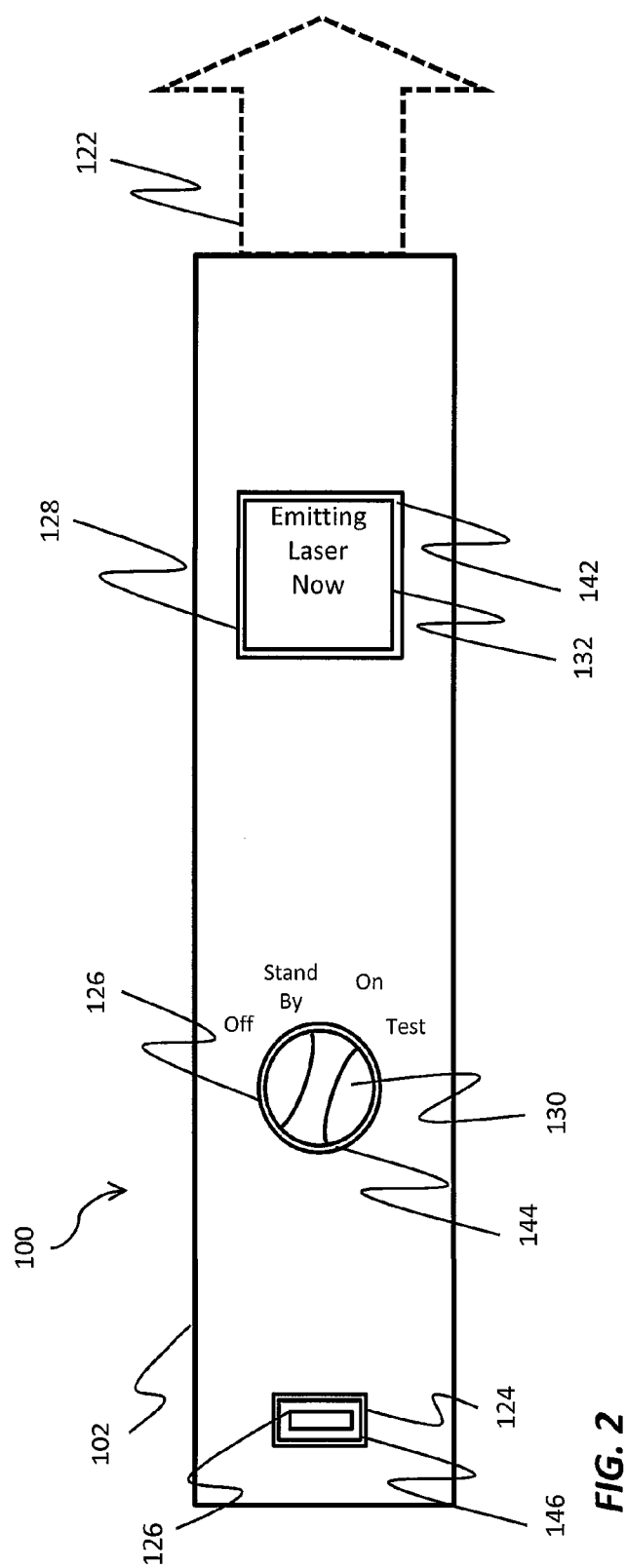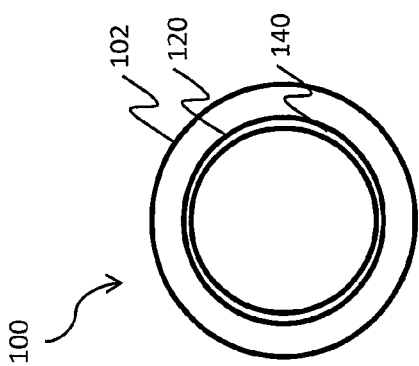
FIG. 2
FIG. 3

LASER SYSTEM WITH REDUCED APPARENT SPECKLE

CROSS-REFERENCE TO RELATED APPLICATIONS

This application claims the benefit of U.S. Provisional Application No. 61/929,762 filed Jan. 21, 2014.

STATEMENT REGARDING FEDERALLY SPONSORED RESEARCH OR DEVELOPMENT

Not applicable.

REFERENCE TO A "SEQUENCE LISTING"

Not applicable.

BACKGROUND OF THE INVENTION

Field of the Invention

The present invention relates to laser systems, and more particularly to laser illuminator systems.

Description of Related Art

Laser illumination systems project a beam of collimated light across an area. Often this is done to enable observation of a laser illuminated area in a particularly useful but limited range of wavelengths. This can be done for example to illuminate an area with light that is not visible to people but that can be detected electronically such as by illuminating an area with near infrared light or short wave infrared light, or this can be done to sense objects in a scene that may be fluoresce when illuminated when exposed to specific wavelengths of light.

One problem with observing laser illuminated areas is while a laser illumination may be generally uniform, non-specular surfaces in the illuminated area may reflect the coherent light from the laser such that interference patterns arise when the light is observed by a person or electronic imager. The interference creates areas that appear to be unnaturally bright and areas that appear to be unnaturally dark creating a high noise component in the reflected light observed in an area. The interference effect is known as speckle.

Speckle is visually distracting and can make it difficult for both human observers and automatic vision systems to detect contrast patterns in the illuminated areas.

Saloma, et al. in a paper entitled "Speckle reduction by wavelength and space diversity using a semiconductor laser", published in Applied Optics, Vol. 29, No. 6, (Optical Society of America 1990) describe a speckle reduction system that uses modulation of a laser to create additional longitudinal modes, with each mode having a different laser frequency. In operation, mode hopping is used and a grating is used to introduce a shift in a position of a point of a source of the illumination as a function of the change in frequency during the mode hopping. The change in position reduces the extent of the speckle contrast when averaged over time.

Trisnadi, in a paper entitled "Speckle contrast reduction in laser projection displays", published in Projection Displays VIII, Ming H. Wu, Editor Proceedings of SPIE Vol. 4657, (SPIE 2002) describes generally speckle reduction strategies as methods for averaging N independent speckle configurations with the spatial and temporal resolution of a detector and identifies three different mechanism for speckle reduction: wavelength diversity which requires a laser with a sufficiently large range of wavelengths to reduce speckle, polarization diversity which requires emission of laser light having two different polarizations and angle diversity which requires shifting the point of illumination. Trisnadi proposes a combination of polarization and angle diversity to achieve speckle reduction. In Trisnadi, angle diversity is accomplished using a moving diffuser.

Geske et al. U.S. Pat. No. 8,743,923 describe the use of a multi-wavelength VCSEL array to reduce speckle using wavelength diversity. In this embodiment, the VCSEL array has a plurality of laser emitters each with a different wavelength creating a laser emitter having a broad enough bandwidth to reduce the speckle effects.

What is need in the speckle reduction art is a solid state laser device that does not require the grating and extended optical path of Saloma, that does not require moving parts like the moving diffuser of Trisnadi and that does not require the complexity and cost of a VSCEL array.

SUMMARY OF THE INVENTION

Laser systems and methods are provided. In one aspect a laser system has semiconductor laser that is adapted to emit a beam coherent light when supplied with an electrical current and driving circuit adapted to supply a first current to the semiconductor laser and to modulate the current supplied to semiconductor across a range of current levels within a determined integration time. The current is modulated so that semiconductor laser will emit light having a first transverse mode structure during a first portion of the range of current levels and a second transverse mode structure during a second portion of the range of current levels causing a shift in the position of a speckle pattern during the integration time that reduces the appearance of speckle.

In another aspect, a method for operating a laser system is provided in which an integration time is determined for an imaging system to be used with the laser system and a current is supplied to a semiconductor laser used in the laser system. The current supplied to the semiconductor laser is modulated across a range of current levels during the determined integration time and the current is modulated so that the semiconductor laser will emit light having a first transverse mode structure during a first portion of the range of current levels and a second transverse mode structure during a second portion of the range of current levels causing a shift in the position of a speckle pattern during the integration time that reduces the appearance of speckle.

BRIEF DESCRIPTION OF THE DRAWINGS

FIG. 2 is a top view of one embodiment of the laser system of FIG. 1.

FIG. 3 is an end view of the embodiment of FIG. 2.

DETAILED DESCRIPTION OF THE INVENTION

Figure 1:
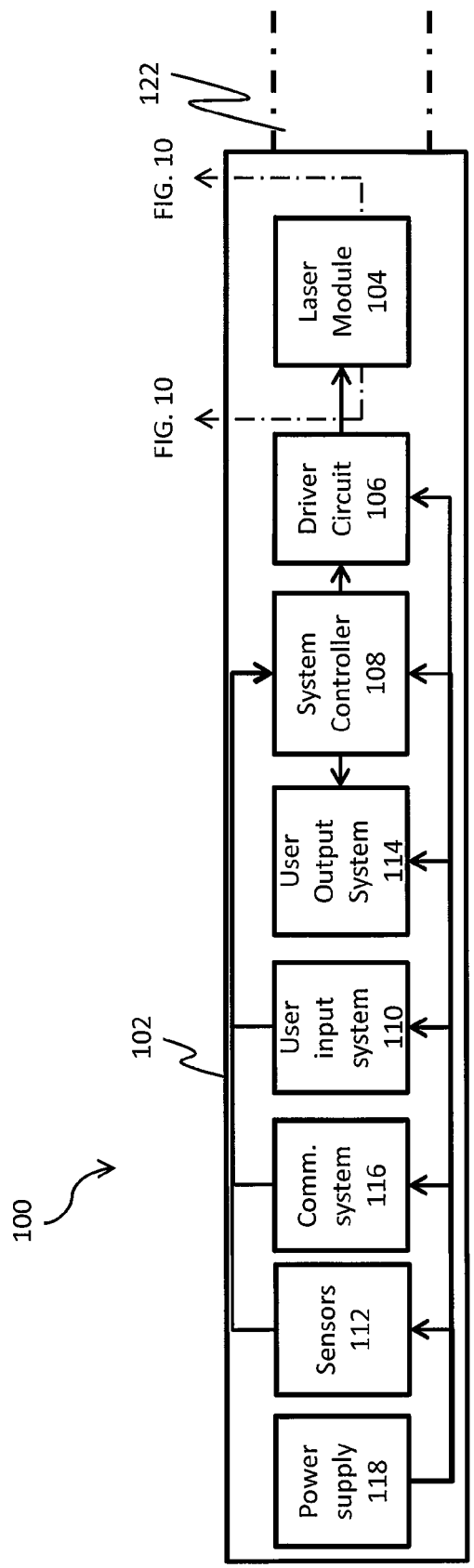
FIG. 1 is a schematic view of a first embodiment of a laser system according to a first embodiment.

FIG. 1 is a schematic view of first embodiment of a laser system 100. FIGS. 2 and 3 illustrate respectively top and end views of the embodiment FIG. 1. In the embodiment illustrated in FIGS. 1-3 laser system 100 has a system housing 102 that encompasses, substantially encloses, or otherwise retains, a laser module 104, a drive circuit 106, a system controller 108, a user input system 110, sensors 112, a user output system 114, a communication system 116, and a power supply 118.

In this embodiment, system controller 108 receives signals from user input system 110, sensors 112, and communication system 116 and determines whether a response to such signals is required. When system controller 108 determines to respond to received signals by causing a laser emission, system controller 108 sends signals to drive circuit 106 causing drive circuit 106 to supply electrical energy from power supply 118 to laser module 104 in a manner that causes laser module 104 to emit a laser beam 122. System controller 108 can also generate signals that cause user output system 114 to generate a human perceptible output. Additionally, system controller 108 can send signals to communication system 116 causing communication system 116 to send signals to other devices, to cause communication system 116 to receive signals from other devices or both. Power supply 118 provides electrical energy to drive circuit 106, system controller 108, user input system 110, sensors 112, user output system 114, and communication system 116. As is shown in FIGS. 1-3, in this embodiment system housing 102 provides an enclosure for each of the components of laser system 100 to provide an enclosed a stand-alone device capable of laser emission.

System housing 102 can be formed of any of a variety of rigid materials such as composites, laminates, plastics or metals. In one configuration, system housing 102 can be formed of an extruded aluminum, thereby providing sufficient strength without requiring significant weight while also providing good thermal transfer properties.

System housing 102 can be fabricated or assembled in any of a variety of ways. In one embodiment, system housing 102 is machined such as by EDM (electrical discharge machining), assembled, or molded if composites, laminates, plastics or metals are employed for system housing 102. System housing 102 also can be fabricated using other conventional techniques including but not limited to additive assembly techniques.

In FIGS. 1-3, system housing 102 is shown having a generally cylindrical profile. However, in other exemplary embodiments, system housing 102 may be configured to provide surfaces that enable system housing 102 to be joined, fixed, held, mounted or otherwise positioned for movement with other devices such as hand-held weapon system 14 or to any of a variety of direct fire weapons such as handheld, side, and small firearms. Such firearms include, but are not limited to, pistols, rifles, shotguns, automatic arms, semi-automatic arms, rocket launchers and select grenade launchers bows. In other embodiments, system housing 102 can be configured to mount any known dismounted or dismounted crew-served weapon, such as machine guns, artillery, recoilless rifles and other types of crew served weapons.

In still other embodiments, system housing 102 can be shaped, sized or otherwise provided in forms that more readily interface with any of a variety of clamping or mounting mechanisms such as a Weaver-style Picatinny rail or dove tail engagement for mounting to these firearms. In further exemplary embodiments, system housing 102 can be configured as a component part of a hand-held weapon system 12 or other direct fire weapon, such as a foregrip, sight or stock.

Drive circuit 106 receives power from power supply 118 and control inputs from system controller 108. In response to the control inputs received from system controller 108, drive circuit 106 generates signals that cause laser module 104 to emit laser light. In the embodiment that is illustrated in FIG. 1 laser module 104 is not directly connected to power supply 118 but rather receives power by way of drive circuit 106 such that drive circuit 106 can control the time, duration, and intensity of electrical energy supplied to laser module 104. Drive circuit 106 may be configured to assist in tuning and/or otherwise controlling the output of laser module 104. Drive circuit 106 can be constructed to provide either pulsed or continuous operation of laser module 104. The rise/fall time of the pulse, compliance voltage and current generated by drive circuit 106 for the laser module 104 are selected based at least in part upon power consumption, heat generation and desired beam intensity considerations. These parameters may also be selected to cause laser module 104 to produce a beam having a desirable wavelength, frequency, transverse mode number and/or other quantifiable characteristics.

Depending on the desired output, drive circuit 106 can enable operation of the laser module 104 as a continuous or pulsed laser, such as by passive, active, or controlled switching. Although specific values depend upon the particular laser module 104 and intended operating parameters, it is contemplated the peak power draw of drive circuit 106 may be between approximately 1 amp and approximately 10 amps, with an average current draw between approximately 0.1 amps and approximately 1.0 amps. As the required voltage may be between on average approximately 9 volts and approximately 12 volts, approximately 0.9 W to approximately 12 W may be consumed. This may represent a substantial power consumption as well as heat generation.

In an exemplary embodiment, drive circuit 106 may assist in controlling and/or modifying the power level of laser module 104 to aid in penetrating components or conditions of the atmosphere through which laser system 100 will direct laser beam 122. Such components or conditions may include, for example, snow, rain, fog, smoke, mist, clouds, wind, dust, gas, sand, and/or other known atmospheric or airborne components. For example, drive circuit 106 can be configured to controllably, manually, and/or automatically increase the current and/or voltage directed to strengthen and/or intensify laser beam 122 emitted by laser module 104 in such conditions.

It is also understood that laser module 104 can have more than one semiconductor laser 180. In one exemplary embodiment of this type, a laser module 104 can have one semiconductor laser 180 in the form of a mid-range adapted infrared quantum cascade laser and another semiconductor laser 180 in the form of a long-range adapted infrared quantum cascade laser. Other combinations of semiconductor lasers 180 are possible.

Alternatively, in other embodiments, laser module 104 can include components that can receive signals from drive circuit 106 and that can adjust power supplied to laser module 104 in response to such signals. In such an alternative embodiment, laser module 104 may receive may receive electrical energy directly from power supply 118.

In the embodiment illustrated in FIGS. 1-3 system housing 102 has plurality of openings shown as openings 120, 124, 126 and 128. In certain embodiments, seals 140, 142, 144, 146 can be supplied to provide a barrier to resist entry of contaminants at openings 120, 124, 126 and 128 so as to protect the components disposed within system housing 102 from water, dust, vapors, or other harmful contaminants commonly experienced in non-controlled environment use. Optionally, system housing 102 can be hermetically sealed, at least in part around laser module 104.

User input system 110 includes human operable sensors such as switches, touch pads, joysticks, audio, video, keypads, key locks, proximity sensors or any other known types of sensors that can detect a user input action and that can provide signals to system controller 108 indicative of the user input action. In the embodiment of FIGS. 1-3, user input system 110 provides a switch 130 that takes the form of a four position mode switch with different settings to enable manual selection of three different operating mode selections and an off selection.

Sensors 112 can include any form of device that can be used to detect or otherwise sense conditions inside or outside of system housing 102 that may be useful to system controller 108 in determining actions to be taken in operating laser system 100. Sensors 112 can include without limitation, light sensors such as photovoltaic cells, contact switches, opto-electronic sensors such as light beam emitter and sensor pairs, electro-mechanical sensors such as limit switches, strain sensors, and proximity sensors such as Hall effect sensors, thermal sensors, meteorological sensors, such as humidity sensors, accelerometers, orientation sensors and other known sensors and transducers.

User output system 114 can include, without limitation actuators, light emitters, video displays, or other sources of human perceptible visual, audio or tactile signals from which a user can determine for example, and without limitation, a status of laser system 100, an operating mode of laser system 100, or that laser system 100 is emitting a laser beam 122 and a characteristics of the laser beam 122 that laser system 100 is emitting or will emit when instructed to do so. In this embodiment, user output system 114 includes a video display 132 that is positioned in opening 128.

Communication system 116 can include any combination of known communication circuits including wired or wireless transponders, transceivers, transmitters, receivers, antennas, modulators, de-modulators, encryption and de-encryption circuits or software and can provide other known components to facilitate data communication, the exchange of control signals or power exchanges in wired or wireless form.

Power supply 118 is shown located within system housing 102. In one configuration, power supply 118 comprises a battery and system housing 102 can include a battery compartment (not shown) sized to operably receive and retain a power supply 118 in the form of batteries. Depending upon the anticipated power requirements, available space, and weight restrictions, the batteries can be N-type batteries or AA or AAA batteries. Additionally, a lithium/manganese dioxide battery such as military battery BA-5390/U, manufactured by Ultralife Batteries Inc. of Newark, N.Y. can be used with laser system 100. The battery-type power supply 118 can be disposable or rechargeable. Battery compartment can be formed of a weather resistant, resilient material such as plastic, and shaped to include receptacles for receiving one or more batteries or other power storage devices. Further, the battery compartment may be selectively closeable or sealable to prevent environmental migration into the compartment or to create a hermetically sealed environment therein.

In other exemplary embodiments, power supply 118 can take the form of a fuel cell, capacitive system or other portable electrical energy storage or generation system. It is understood that any type of power supply 118, preferably portable and sufficiently small in size can be utilized.

As is noted above, system controller 108 drives operation of laser system 100 and receives signals from user input system 110, sensors 112 and communication system 116 that system controller 108 can use to control operation of laser system 100. System controller 108 comprise for example a computer, a microprocessor, micro-controller, programmable analog logic device or a combination of programmable or hardwired electronic devices capable of performing the functions and actions described or claimed herein.

In the embodiment of FIGS. 1-3 system controller 108 determines a mode of operation of laser system 100 in response to a position of switch 130. When switch 130 is positioned in the "Off" position, user input system 110 sends signals to system controller 108 causing system controller 108 to remain in an inactive state or can maintain a low power consumption mode of operation.

However, when system controller 108 receives signals from user input system 110 indicating that switch 130 has been moved to the "On" position system controller 108 can generate signals causing drive circuit 106 to drive laser module 104 to generate laser light. In other embodiments, switch 130 can comprise a switch that provides power to initiate operation of system controller 108 only when switch 130 is in a position other than the "Off" position.

Other modes of operation are possible. For example a "Stand By" mode of operation can be provided to conserve stored energy of from power supply 118 while maintaining the laser system 100 in an advanced state of readiness for use. For example, when switch 130 is moved to the "Stand By" position user input system 110 can send signals to system controller 108 from which system controller 108 can determine that this mode of operation has been selected.

In one embodiment, system controller 108 can detect that switch 130 has been moved to the "Stand By" position and can respond to this by sending signals to drive circuit 106 causing drive circuit 106 to begin supplying power circuits or subsystems, if any, that require some time to reach a state where they are ready for immediate activation when switch 130 is moved to the "On" position. Not all circuits or subsystems will need be activated at such times and a stand by option relieves the operator from being confronted with the choice of operating the laser system 100 in a high power consumption "On" mode prior to the need to do so and the choice of holding the device in the "Off" state to conserve power with the understanding that there will be a lag time before activation.

Additionally, in the embodiment of FIGS. 1-3 switch 130 can be positioned at a location that indicates that laser system 100 is to be operated in a "Test" mode. In one example of this type system controller 108 can cause laser module to emit a lower powered laser beam 122. This lower powered laser beam can 122 be used to allow verification of the operational status of laser system 100 such as by emitting a lower powered laser test beam that can be directed at, for example, nearby targets for training purposes or at target strips or pages that change in appearance when illuminated by the laser in the test mode. Here too, this mode will be entered when system controller 108 receives a signal from user input system 110 indicating that switch 130 has been moved to a position selecting the "Test" mode.

Figure 4:
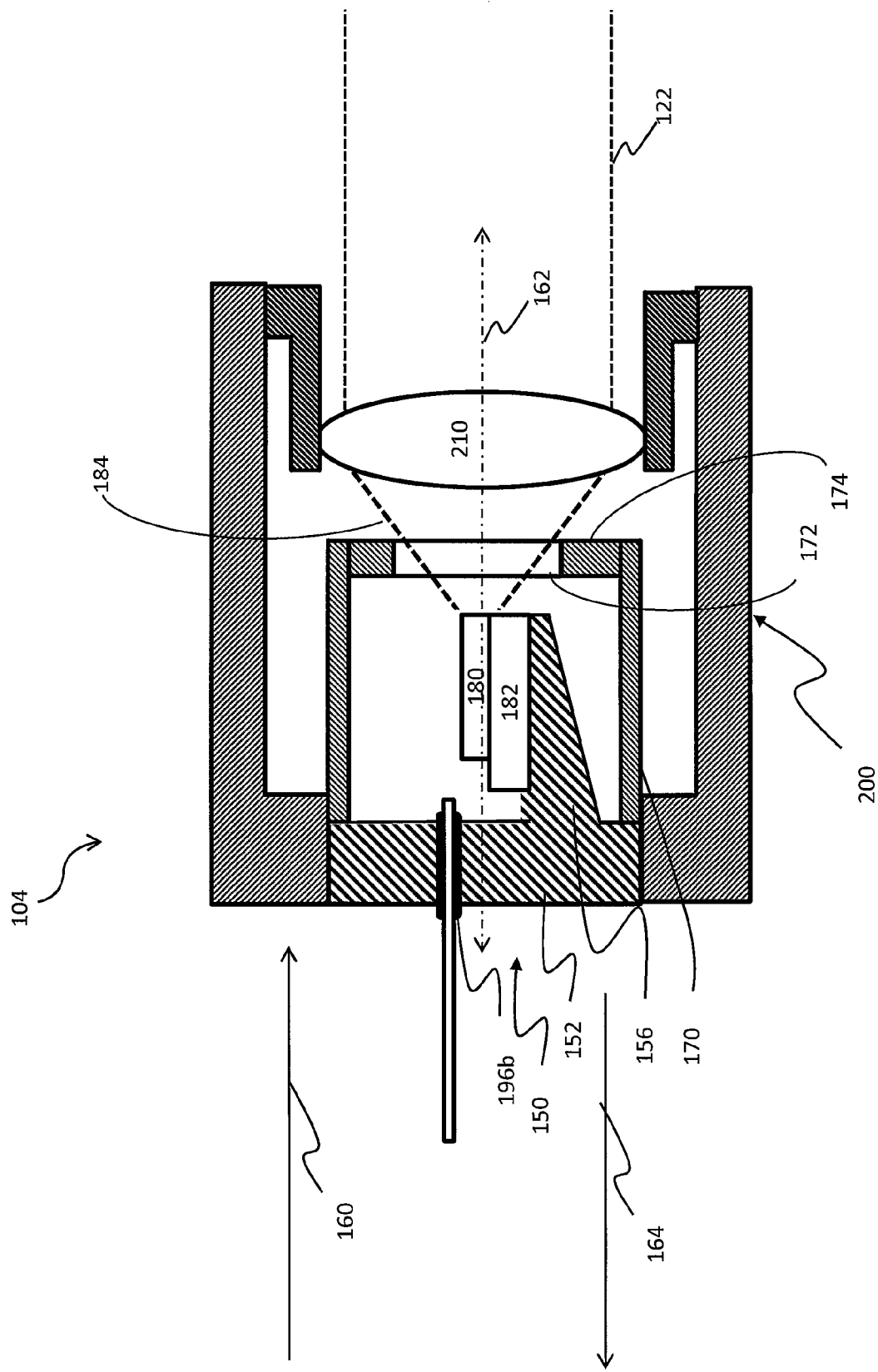
FIG. 4. is a side section of the embodiment of FIGS. 1-3.

Turning now to FIG. 4 what is shown is a cross-section schematic view of one embodiment of a laser module 104 taken as shown in FIG. 1. In the embodiment that is illustrated in FIG. 4, laser module 104 has a laser core 150 with a base 152 having a front side 154 from which a header 156 extends in a first direction 160 and a housing 170 shaped to combine with front side 154 to form a sealed environment about header 156.

A semiconductor laser 180 is mounted to header 156. In this embodiment, semiconductor laser 180 is mounted to header 156 by way of a submount 182 and is positioned to direct a divergent laser light 184 in first direction 160 through a window 172 on a front portion 174 of housing 170. Semiconductor laser 180 or submount 182 can be joined to header 156 in any of a variety of ways including conventional fasteners, solders, conductive adhesives and the like. Semiconductor laser 180 in turn is typically bound to submount 182 using soldering techniques, although other techniques are also known.

Semiconductor laser 180 can comprise for example, any semiconductor device that can emit a laser output. Examples of semiconductor laser 180 include but are not limited to a diode laser, quantum cascade lasers, inter-band cascade lasers. These types of semiconductor lasers 180 share generally the characteristics of being made from a semiconductor material and having a emitting a divergent laser light beam while also generating a meaningful amount of heat that must be dissipated to protect semiconductor laser 180.

In the embodiment illustrated in FIG. 4, semiconductor laser 180 emits a divergent laser light 184 having a wavelength in the infrared region such as between 2μ and 30μ wavelength. However, in other embodiments, semiconductor laser 180 can emit a divergent laser light 184 having any of a wide range of wavelengths including but not limited to ultraviolet wavelengths, visible wavelengths, and near infrared wavelengths. For the purposes of the following discussion, it will be assumed that in the embodiment of FIG. 4, semiconductor laser 180 is a quantum cascade type laser.

A frame 200 is joined to base 152 and extends from base 152 past window 172 to position a lens 210 at a distance along axis 162 from semiconductor laser 180. In operation, semiconductor laser 180 generates a divergent laser light 184 which is directed toward lens 210. Lens 210 collimates the divergent laser light 184 from semiconductor laser 180 into a laser beam 122 when positioned at a location where lens 210 can effectively focus light from semiconductor laser 180. As used herein a laser beam 122 includes a laser beam that is fully collimated as well as laser beams having substantial collimation with a limited allowable divergence.

In general, lens 210 controls the field of illumination provided by divergent laser light 184. This field of illumination can be narrow so as to concentrate divergent laser light 184 to create a field of illumination at a distant target or it can be made even more narrow to provide pointing, marking or designation spots of high intensity. Lens 210 can comprise one or more lenses and lens systems and can be adjustable between multiple configurations to provide different degrees of collimation.

Lens 210 is most effective when held within a preferred range of positions from semiconductor laser 180. However, in practical use this is difficult to achieve with a static lens mounting design. In particular it will be understood that a variety of forces can conspire to influence the distance that a mechanical system such as frame 200 will position lens 210. Chief among these are the forces of thermal expansion and contraction which can cause significant changes in the length of components of frame 200 and the resultant position of lens 210 relative to semiconductor laser 180.

In this embodiment, frame 200 is optionally of an athermalized design meaning that frame 200 is designed so that frame 200 will hold lens 210 in a desirable range of positions relative to semiconductor laser 180 despite any thermal expansion or contraction of any components of frame 200 that may arise during transport and operation of laser system 100. Such systems do not seek to completely resist or prevent heating or cooling of frame 200, but rather are defined to provide mechanisms to allow for automatic compensation for any thermal expansion caused by such heating or cooling.

Optionally, frame 200 can be configured to allow a user to adjust the degree of collimation of divergent laser light 184 so as to form a beam output 122 having a divergence that is within a range of divergences. This adjustability can allow laser system 100 to be used for a variety of functions including but not limited to illuminating a relatively nearby field of view and a relatively distant field of view, and proving a highly collimated beam for designating, marking or pointing purposes.

Figure 5:
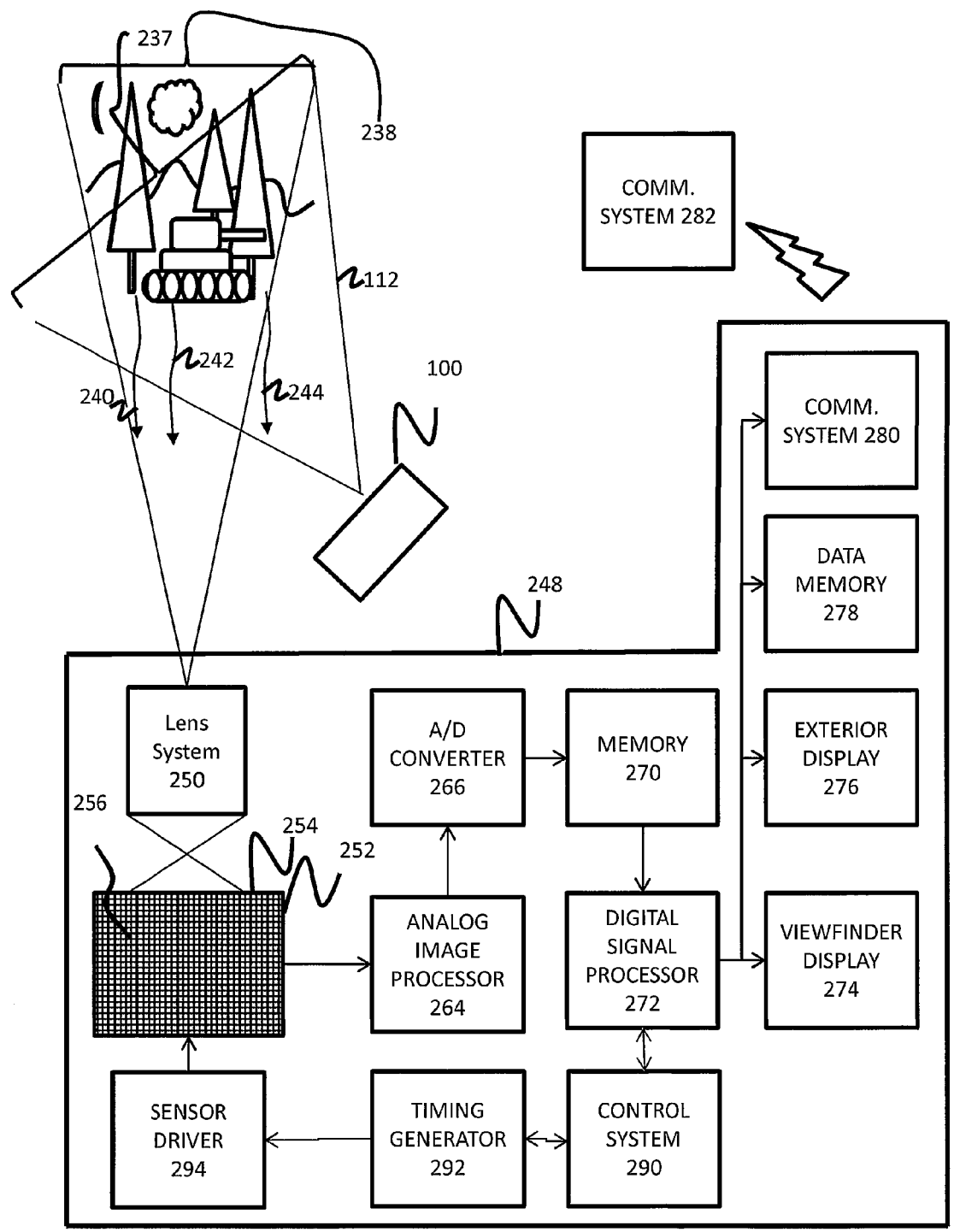
FIG. 5 shows a first embodiment of a laser system, an imaging system and a field of view.

As is shown in FIG. 5, laser beam 122 from laser system 100 illuminates a field of illumination 237 and light 240 can reflect therefrom in a specular fashion or by way of scattered reflection, be absorbed thereby or be absorbed and re-emitted thereby 242. Additionally, field of view 238 may have portions thereof that emit or reflect light 244 other than that provided by laser beam 122 and that are at or near wavelengths to those emitted by the illuminator or that can otherwise be sensed by a thermal imaging system such as thermal imaging system 248.

FIG. 5 one exemplary embodiment of a thermal imaging system 248 having an optional lens system 250 and a thermal imager 252. Lens system 250 focuses light from a field of view 238 to form an image onto thermal imager 252. Thermal imager 252 is configured to sense a range of wavelengths of light including wavelengths of light emitted by laser system 100. As is illustrated here, field of illumination 237 and field of view 238 at least in part overlap.

Thermal imager 252 may be any device or combination of devices configured to receive such reflected light 240, re-emitted light 242 and other light 244. Conventionally, thermal imager 252 has an imaging surface 254 with an array of radiation sensors 256. In a typical configuration, individual radiation sensors 256 are each capable of generating a signal that is representative of an amount of radiation incident on the radiation sensor 256 within a period of time known as an integration time. In one embodiment, thermal imager 252 may comprise an array of radiation sensors 256 in the form of microbolometers or other like sensors. In other embodiments, radiation sensor may 254 may comprise any type of known semiconductor image sensing array such as specially doped CMOS image sensors. Other known image sensing technologies that can be used to determine the amount of radiation incident at a plurality of positions on a focal plane can be used.

Typically, radiation sensors 256 generate an analog output signal. The analog output of each is optionally amplified by an analog amplifier (not shown) and analog processed by an analog signal processor 264 to reduce any output amplifier noise of image sensor 252. The output of analog signal processor 264 is converted to a captured digital image signal by an analog-to-digital (A/D) converter 266.

The digitized image signal is optionally temporarily stored in a memory 270, and is then processed using a programmable digital signal processor 272. Digital signal processor 272 creates digital images of the field of view 238. These digital images can be adapted for display on, for example, a viewfinder display 274 or other exterior display 276. Viewfinder display 274 and exterior display 276 can comprise, for example, a color liquid crystal display (LCD), organic light emitting display (OLED) also known as an organic electroluminescent display (OELD) or other type of video display or any other known form of video image display. Alternatively, a communication system 280 can be used to send the digital images to an external device 282 such as a wirelessly connected viewfinder, a targeting system, remote signal analysis systems or viewing or control equipment at a remote command and control center.

Optionally, digital signal processor 272 uses the initial images to create archival images of the scene. Archival images are typically high resolution images suitable for storage, reproduction, and sharing. Archival images are optionally compressed using the PEG standard and stored in a data memory 278.

In operation, control system 290 sends signals to a timing generator 292 indicating that images are to be captured. Timing generator 292 can provide signals that can be used by various elements of thermal imaging system 248 to control image capture, digital conversion, compression, and storage operations. Thermal imager 252 is optionally driven from timing generator 292 by way of an image sensor driver 294. Control system 290, timing generator 292 and image sensor driver 294 cooperate to cause image sensor 252 to determine an amount of radiation incident on each of radiation sensors 256 across an integration time that is either fixed or variable. After the integration time is complete an image signal is provided to analog signal processor 264 having analog signals indicative of the radiation sensed at each of radiation sensors 264 during the integration time. These analog signals are processed as described in greater detail above.

The ability of a radiation sensor 256 to generate a signal that is representative of the amount of radiation incident on the radiation sensors during an integration time is not infinite. Instead, the ability of a radiation sensor 256 to sense radiation is limited by a lower response threshold and an upper response threshold. The lower response threshold can be, for example, an exposure level at which the inherent signal to noise properties of a radiation sensor 256 and the electronic circuitry designed to extract signal information from radiation sensor 256 approaches a threshold signal to noise ratio of the exposing radiation. Accordingly, when radiation sensor 256 is exposed to radiation that is below the lower response threshold, it becomes difficult to ensure that the signal received from the radiation sensor 264 accurately represents the relative intensity of radiation incident on the sensor within the integration time.

Similarly, the upper response threshold is the light exposure level where it becomes difficult to ensure that the signal received from a radiation sensor 256 accurately represents the relative intensity of the radiation incident on radiation sensor 256 within the integration time.

It will be appreciated that more image detail can be visually obtained from a captured image that includes large contrast differences. Such large contrast differences are lost however, when an image includes a large proportion of image information from radiation sensors 256 that have been exposed to light above the upper threshold or below the lower threshold. Accordingly, integration times are typically adjusted to help ensure that radiation sensors 264 are exposed to radiation that is generally between a lower threshold and an upper threshold for the radiation sensors. However, in some low radiation scenes, such as at night there may be insufficient ambient illumination to allow image capture without a signal to noise ratio in the image that is too high to allow for accurate observation of a field of view. Illumination of the field of view is therefore required.

Lasers are appropriate for illumination purposes particularly where it is desirable to project illumination at distance down range and within controllable wavelengths. However lasers themselves may introduce noise into the field of view. Of particular concern, is a condition known as speckle. Speckle arises when coherent light reflects from more than one different point in a field of view 238 in a manner that coherently combines at a point of observation.

Figure 6:
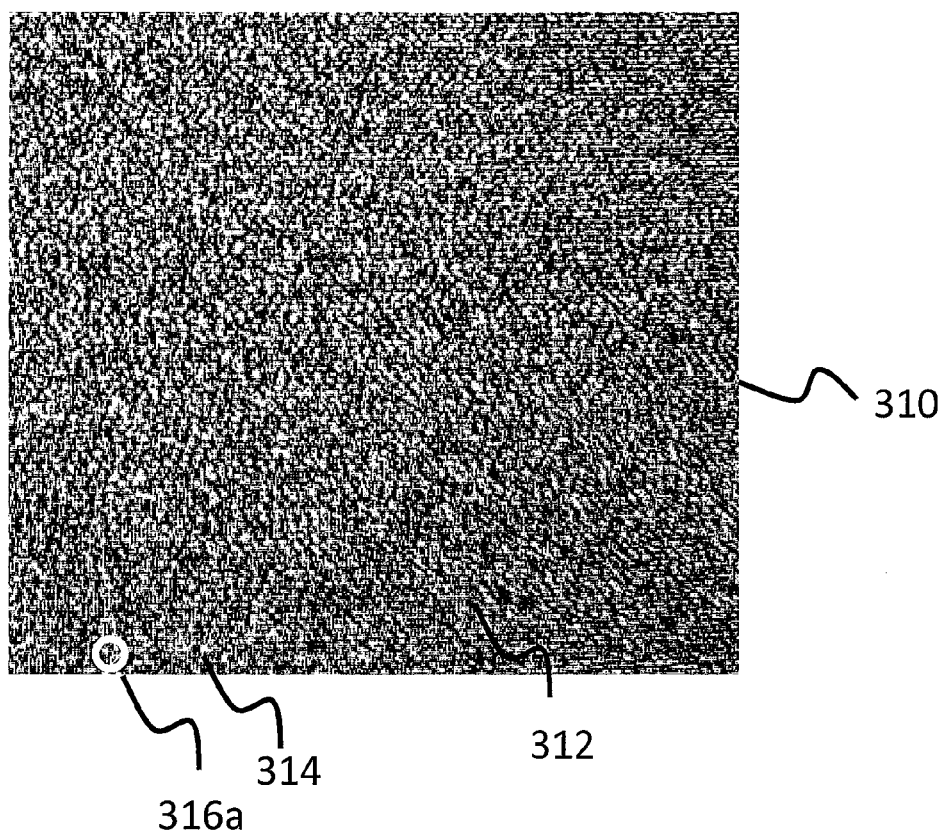
FIG. 6 shows a speckle pattern.

FIG. 6 illustrates one hypothetical example of a speckle pattern that may exist in a field of view of a sensor 252. Speckle is typically observed as a pattern 310 of darker spots such as darker spot 312 and lighter spot such as lighter spot 314 in a uniformly laser illuminated field of view 238 having at least one rough surface. Typically, the speckle pattern 310 for a given field of view is generally static while observation and illumination remain constant.

It will be appreciated that such a pattern 310 of speckle can make it particularly difficult to determine the differences between contrast patterns in the image that are a product of the objects in field of view 238 and contrast patterns in the image that are a product of speckle.

Figure 7:
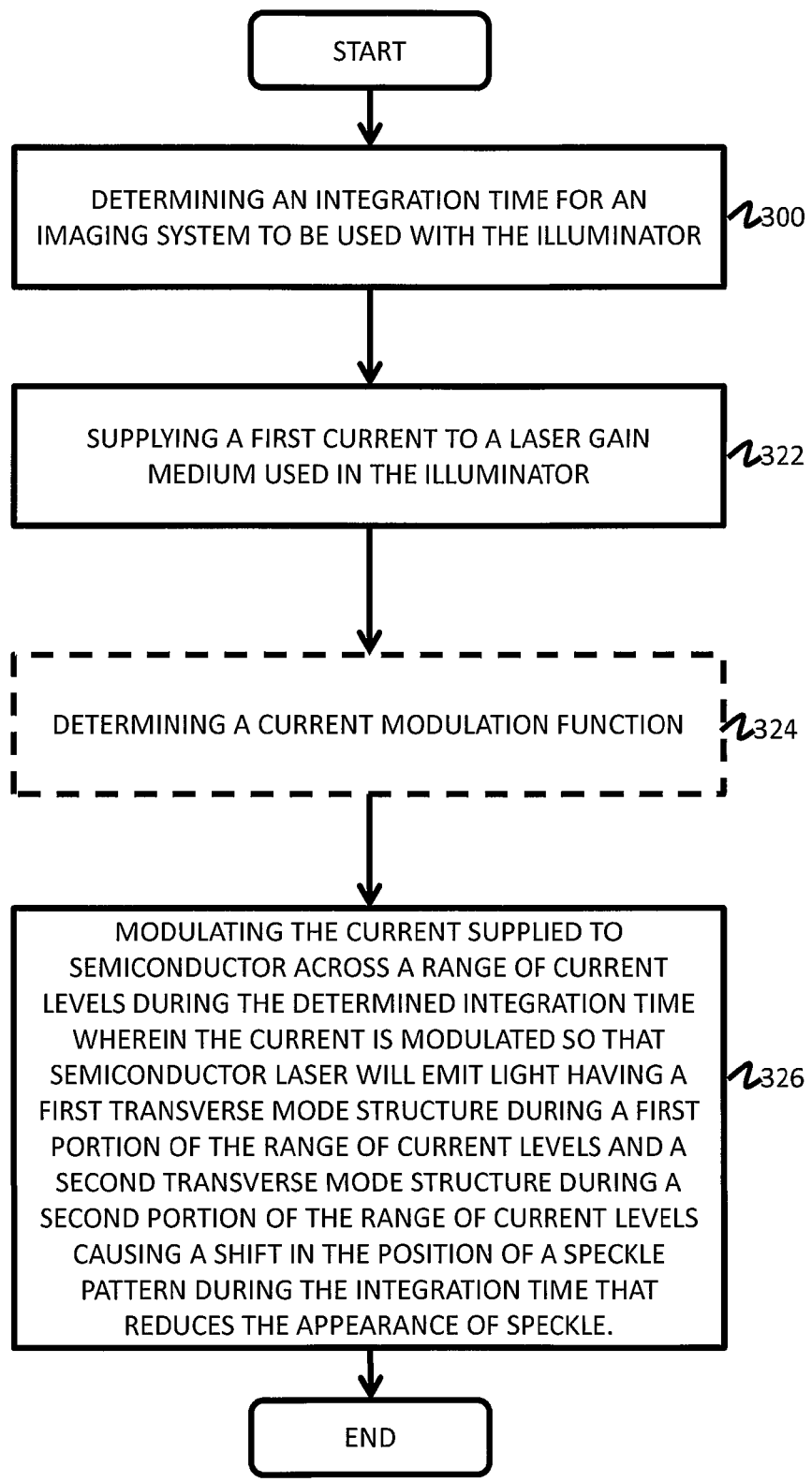
FIG. 7 shows a flow chart of one method for operating a laser system.

However, laser system 100, unlike the illuminators of the prior art is adapted to operate in a manner that reduces the appearance of speckle in the field of view 238. FIG. 7 illustrates a flow chart of a method by which this is done.

As is shown in FIG. 7, in this embodiment, an integration time is determined for an imaging system 248 that is to be used with laser system 100 (step 320). In certain embodiments, the integration time can be predetermined such as where it is known that laser system 100 will be used with a specific imaging system 248 or where it is known that laser system 100 will be used under certain conditions that require a specific integration time. The integration time or parameters that may be related to the integration can also be user entered or selected by way of user input system 110. In other embodiments, integration time can be determined automatically by communication between laser system 100 and imaging system 248. For example, communication system 280 of imaging system 248 can communicate with communication system 116 so control system 290 can provide data from which an integration time used by thermal imaging system 248 can be determined.

A first current is then supplied to semiconductor laser 180 sufficient to cause semiconductor laser 180 to emit a beam of laser light 184 having a first transverse mode structure (step 322).

The current applied to semiconductor laser 180 is then modulated across a range of current levels during the determined integration time (step 326). The modulation of the current is determined so that semiconductor laser 180 will emit light having a first transverse mode structure during a first portion of the range of current levels and a second transverse mode structure during a second portion of the range of current levels. A change in transverse mode structure may take the form of a change in the number of transverse modes or the relative portion of the overall intensity of a laser beam 122 formed by individual ones of more than one simultaneously emitted transverse modes.

Laser beam 122 has an angular emission profile that is a function of the transverse mode structure. The direction of higher intensity emissions in the angular emission profile change with the transvers mode structure. This changes the relative angle of incidence of an illuminating light on the field of illumination 237 shifting the speckle pattern as will now be described in greater detail with reference to FIGS. 8-10.

Figure 8:
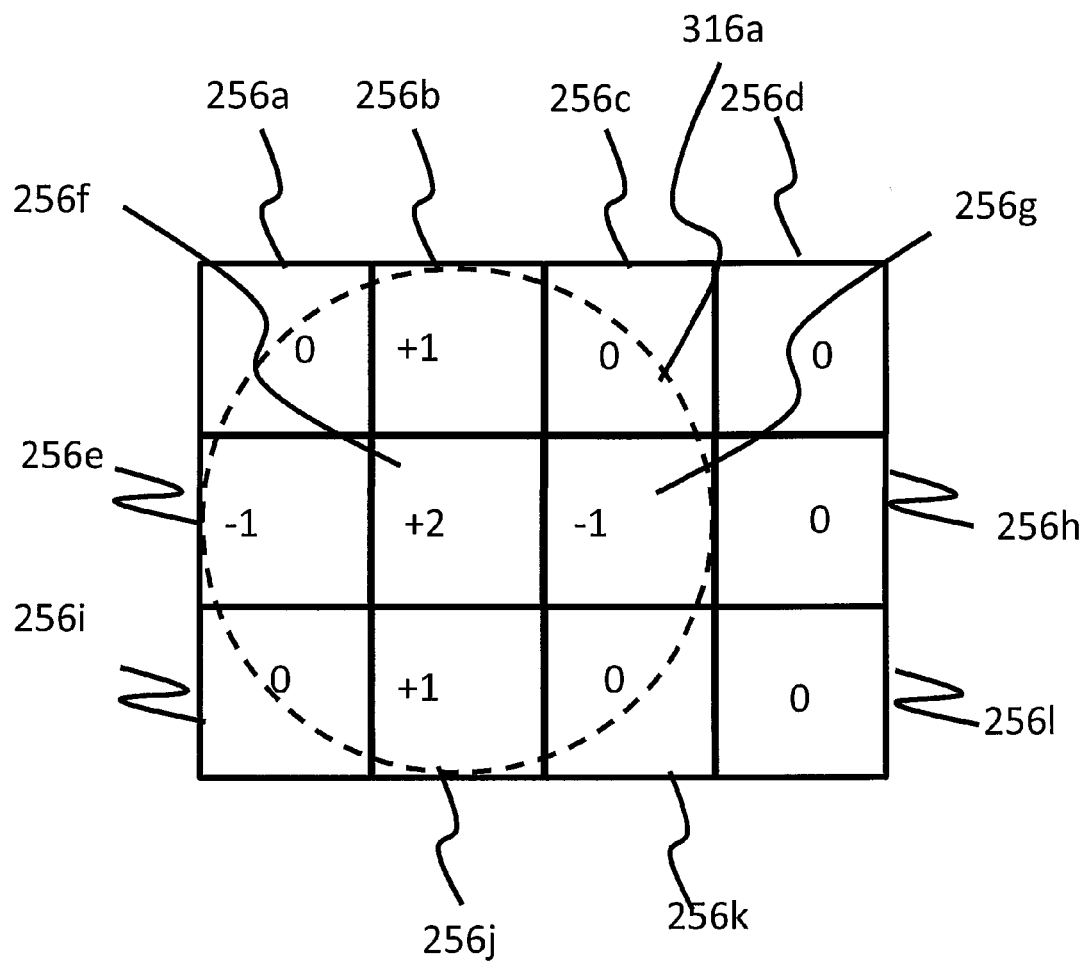
FIG. 8 shows a portion of the speckle pattern on a plurality of radiation sensors.

FIG. 8 shows a first example of a plurality of radiation sensors 256a-256k on which a portion 316a of speckle pattern 310 is formed as shown in FIG. 6. Portion 316a represented in FIG. 8 by numerical pattern of positive and negative numbers. This pattern of positive and negative numbers are representative of the intensity variation at each radiation sensors 256a-256k due to portion 316a of speckle pattern 310. Positive numbers are used to denote radiation sensors 256 on which coherent light from field of view 238 combines to increase the amount of light incident on a radiation sensor 256 during an integration time. Negative numbers are used to denote radiation sensors 256 on which coherent light from field of view 238 combines to decrease the amount of light incident on a radiation sensor 256 during an integration time. Different integers are used to represent potential intensity differences in the light sensed by radiation sensors 256a-256k during an integration time caused by the speckle.

Figure 9:
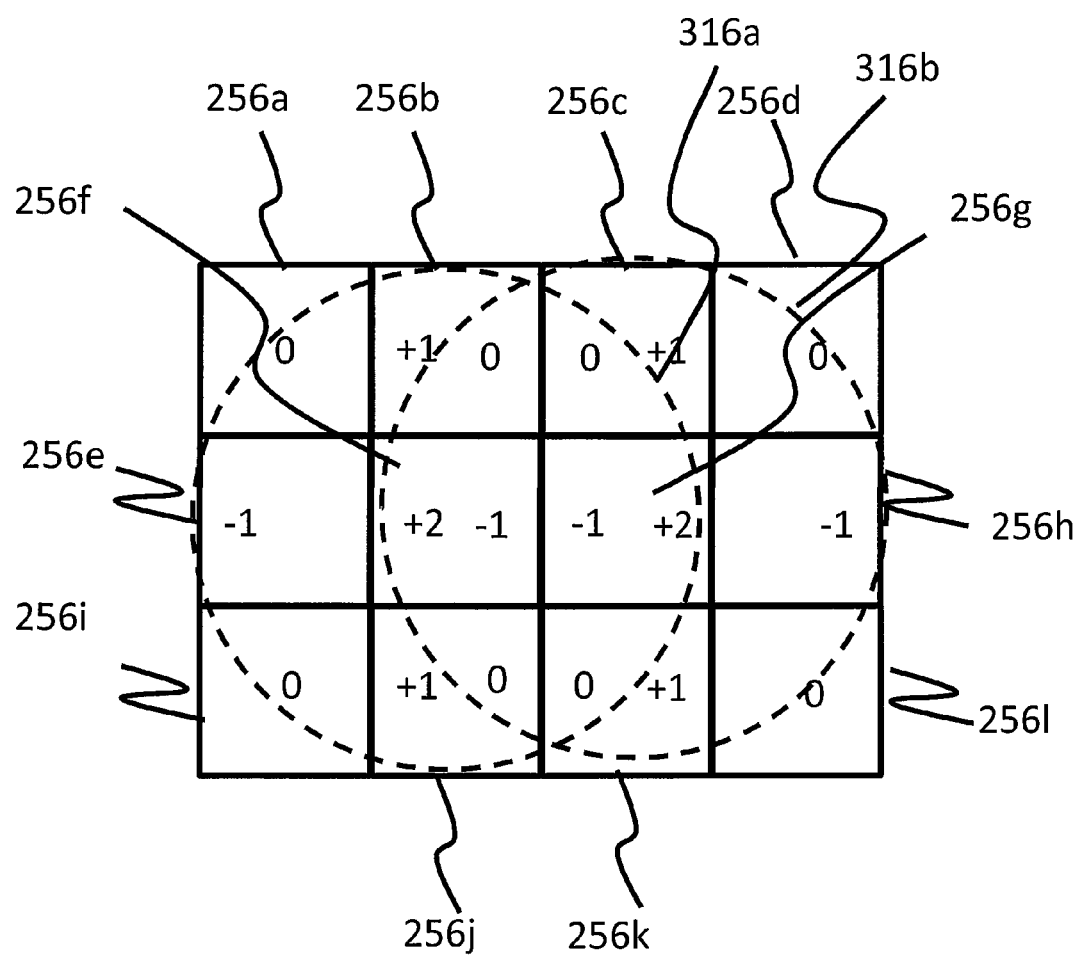
FIG. 9 shows the portion of FIG. 8 in combination with a shifted portion of the speckle pattern.

As is also shown in FIG. 9, when the current supplied semiconductor laser 180 transitions from the first range of current levels to the second range of current levels semiconductor laser 180 generates a divergent laser light 184 having a different transverse mode structure. This causes the speckle pattern 310 to shift, in this embodiment to the right, such that portion 316a is repositioned as shown as portion as illustrated in FIG. 9.

Figure 10:
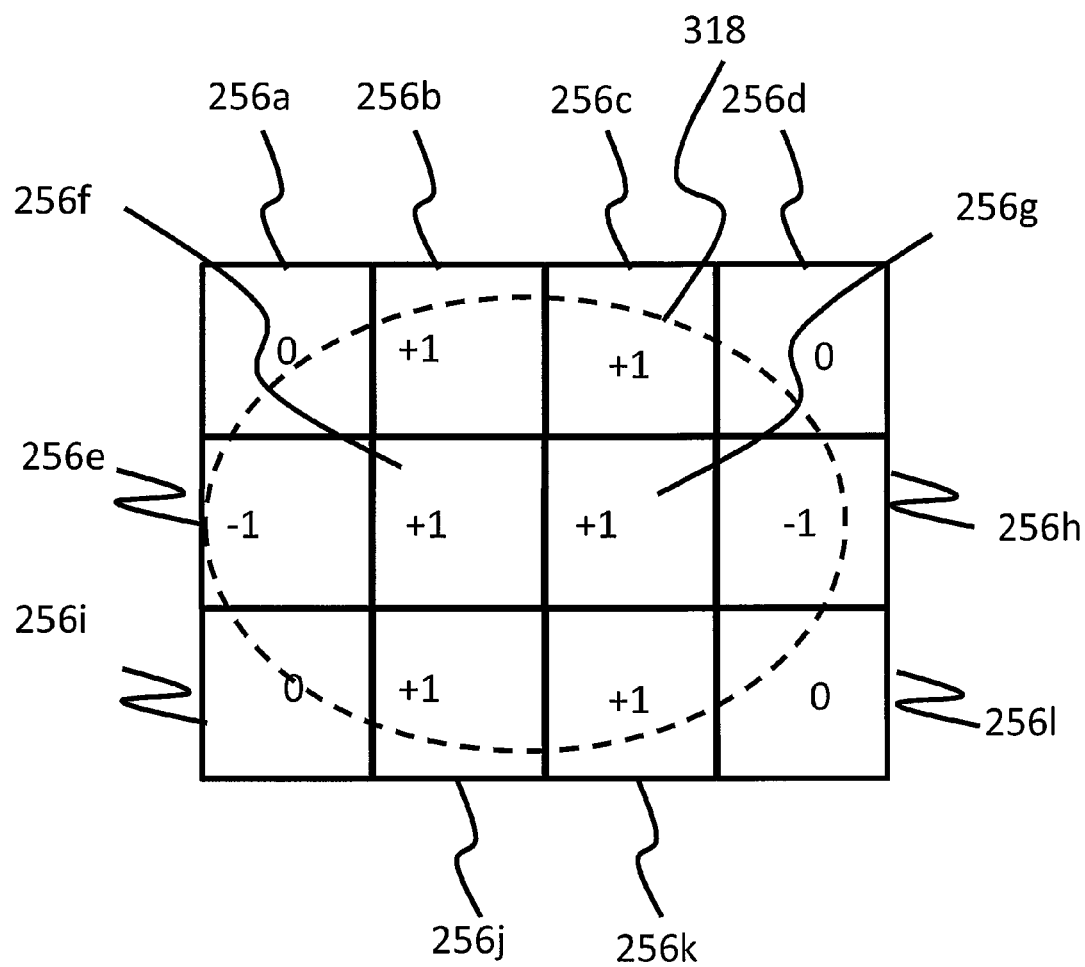
FIG. 10 shows the net effect of the shift on the plurality of radiation sensors.

As is shown in FIG. 10, this shift has a number of effects net effects over the integration time. For example, radiation sensors 256b and 256c, 256j and 256k experience a modest increase in sensed radiation over the integration time while radiation sensors 256e and 256h experience a modest decrease in sensed radiation. Radiation sensors 256f and 256g experience a modest net increase in sensed radiation despite receiving light at a bright spot in the portion 316a/b of speckle pattern 310 at least during part of the integration time.

Figure 11:
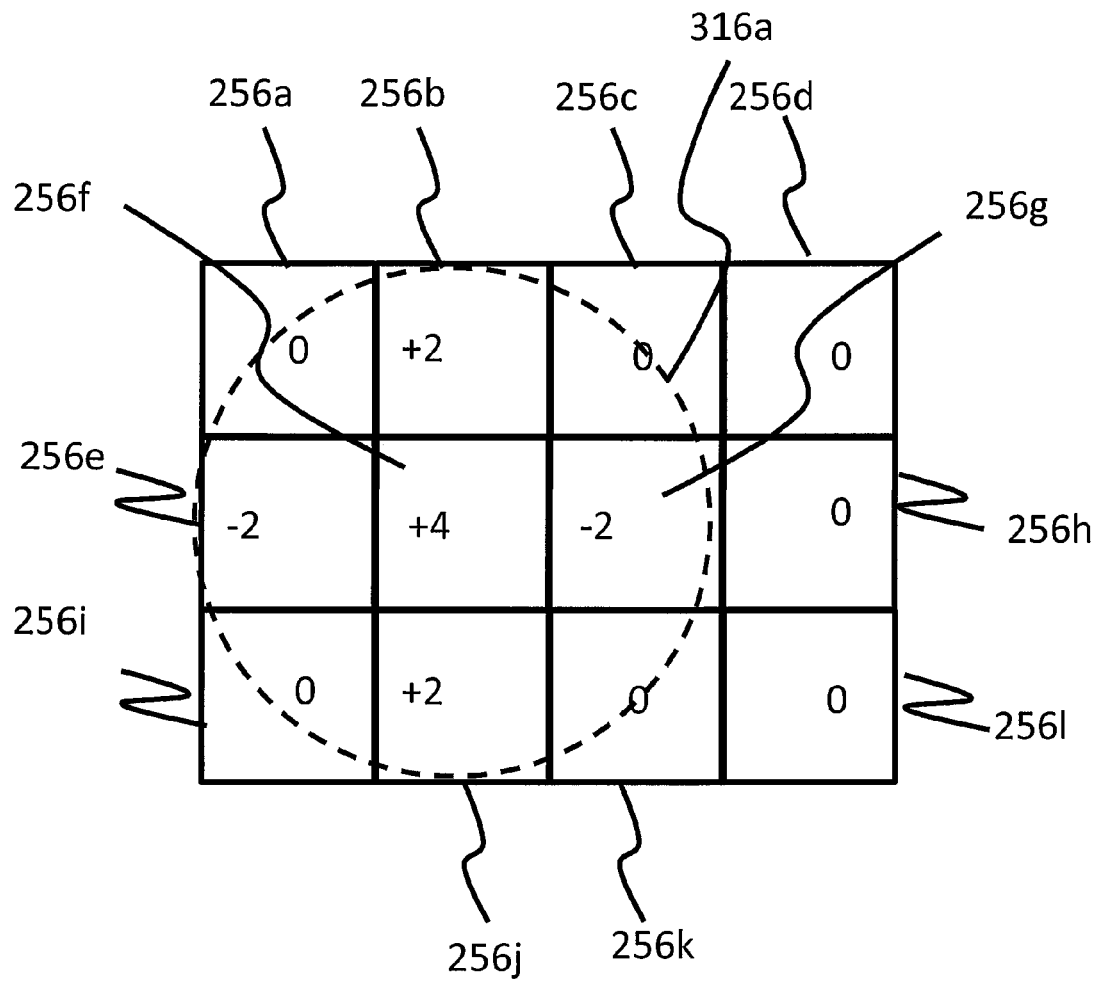
FIG. 11 shows the effect of unshifted speckle on the plurality of radiation sensors as is known in the prior art.

By way of comparison, FIG. 11 illustrates the net effects of portion 316a of speckle pattern 310 on radiation sensors 256a-256k using a prior art laser illumination system that does not provide the changing the transverse mode structure. As can be seen from this, portion 316a causes a speckle pattern over the integration time that has much higher absolute intensities as well as having greater relative differences between brighter areas and darker areas such as between radiation sensor 256f and 256g.

It will be appreciated that by shifting the structure of transverse modes in laser beam 120 illuminating at least a part of field of view 238 during the integration time of imaging system 248 the impact of speckle is averaged across multiple radiation sensors and the relative impact of speckle is greatly reduced.

In some embodiments, a ridge width or distance between transverse sidewalls of an active region in a semiconductor laser 180 is selected to provide transverse mode structures that are different when energized in at least two different ranges of current in order to provide the desired shift. For example, a ridge with a width of between about 1 and 2 wavelengths of a light emitted as a laser beam 122 by semiconductor laser 180 can be used for this purpose.

Additionally, the selection insulating material adjacent to transverse sidewalls of an active region in a semiconductor laser 180 is used to facilitate transitions in transverse mode structures to provide the desired shift. For example, semi-insulating materials such as indium phosphide can be used to achieve transverse mode structures having a first characteristics, while di-electric materials such as silicon dioxide or silicon nitride can be used to achieve transverse mode structures having second characteristics that are different from the first characteristics. In some embodiments the use of di-electric materials can more effectively lead to a change in transverse mode structure than the use of semi-insulating materials such as indium phosphide on semiconductor lasers having equal ridge widths.

In addition, the thickness of the semi-insulating material in the presence of a metal or a semi-conductor on the outside of the semi-insulating material can also be used to influence the characteristics of the transverse mode structure.

Returning to FIG. 7 it will be appreciated that the method can include the optional step of determining a modulation function (step 324). The modulation function can define the amplitude and time rate of change of the current supplied to semiconductor laser 180. The modulation function can also define a shape of the waveform used in modulation. In some embodiments, the modulation frequency used to apply current into semiconductor laser 180 may induce temperature changes within semiconductor laser 180 such that different transverse mode structures can be reached based as a product of heating and cooling of the semiconductor laser 180 within the integration time. Such heating and cooling may occur to a greater extent in response to lower frequency modulation while occurring to a lesser extent in response to higher frequency modulation.

As is noted above, semiconductor laser 180 can take the form of a laser that emits light between 2 um and 30 um. However, specific wavelengths of light within this range may be particularly useful for achieving desired results such as illumination over a particular ranges. Conventionally selection of a semiconductor laser 180 for use in illuminating applications and in particular in illuminating applications over particular ranges has been made based primarily on the transmission efficiency of the laser in expected environmental conditions.

This would suggest that different types of semiconductor lasers 180 emitting different wavelengths are necessary for similar applications and that the selection of semiconductor laser 180 should be made based upon anticipated use cases. This leads to unnecessary redundancy, reduced overall performance and expense.

Instead, the inventor has discovered that a system approach to selecting semiconductor lasers 180 for use in applications such as long range illumination can yield superior results. In particular, the inventor notes that the fundamental upper power limit of semiconductor lasers 180 having certain wavelengths is greater than that of semiconductor lasers 180 having other wavelengths. For example, the fundamental upper power limit of semiconductor lasers 180 having a wavelength of about 4.0 um is substantially lower than the fundamental upper power limit of semiconductor lasers having a wavelength of greater than 4.6 um. This power advantage can offset or nearly offset the efficiency advantages provided by lower powered semiconductor lasers 180 at all but the most extreme environmental conditions. Additionally in some circumstances efficiency advantages of lower powered laser system can be completely offset where, for example, sensing equipment such as imaging systems 248 are more sensitive to wavelengths that are greater than about 4.6 um than other wavelengths.

It will be appreciated from this that selection of semiconductor lasers 180 for particular applications or groups of applications can be based upon the response of imaging system 248 including optics such as lens system 250, or filters or other optical components, the atmospheric transmission characteristics, and the output power of semiconductor laser 180.

The drawings provided herein may be to scale for specific embodiments however, unless stated otherwise these drawings may not be to scale for all embodiments. All block arrow representations of heat flow are exemplary of potential thermal patterns and are not limiting except as expressly stated herein.

The invention has been described in detail with particular reference to certain preferred embodiments thereof, but it will be understood that variations and modifications can be effected within the spirit and scope of the invention.

The invention claimed is:

1. A laser system comprising:
   a semiconductor laser adapted to emit a beam of coherent light when supplied with an electrical current; and
   a driving circuit adapted to supply a current to the semiconductor laser and to modulate the current supplied to the semiconductor laser within a determined integration time during which radiation including radiation caused by the coherent light is captured by an electronic imager of imaging system to form an image;
   wherein the current is modulated so that the semiconductor laser will emit light having a first output intensity and a first transverse mode structure during a first modulation and a second transverse mode structure having substantially the first output intensity during a second modulation causing a shift in a position of a speckle pattern during the integration time that reduces the appearance of speckle in the captured image.

2. The system of claim 1, wherein a change in transverse mode structure takes the form of a change in the number of transverse modes in the laser beam.

3. The system, of claim 1, wherein the change in transverse mode structure comprises a change in the relative portion of the overall intensity of a beam formed by individual ones of more than one simultaneously emitted transverse modes.

4. The system, of claim 1, wherein the laser beam has an angular emission profile that is a function of the transverse mode structure and wherein the direction of higher intensity emissions in the angular emission profile change with the transverse mode structure.

5. The system of claim 1, wherein the laser has a ridge width selected to provide transverse mode structures that are different when energized in at least two different ranges of current in order to provide the shift in transverse mode structure.

6. The system of claim 5, wherein the ridge width is between about 1 and 2 wavelengths of a light emitted as a laser beam by the semiconductor laser.

7. A method for operating a laser system comprising:
   determining an integration time for an imaging system to be used with the laser system during which radiation including at least one of reflected coherent light and re-emitted coherent light is captured by an imager to form an image;
   supplying a current to a semiconductor laser used in the laser system; and
   modulating the current supplied to the semiconductor laser during the determined integration time;
   wherein the current level is modulated so that the semiconductor laser will emit light having a first output intensity and a first transverse mode structure during a first modulation and will emit light having substantially the first output intensity and a second transverse mode structure during a second modulation causing a shift in the position of a speckle pattern during the integration time that reduces the appearance of speckle in the captured image.

8. The method of claim 7, wherein a change in transverse mode structure takes the form of a change in the number of transverse modes in the laser beam.

9. The method of claim 7, wherein the change in transverse mode structure comprises a change in the relative portion of the overall intensity of a beam formed by individual ones of more than one simultaneously emitted transverse modes.

10. The method of claim 7, wherein the laser beam has an angular emission profile that is a function of the transverse mode structure and wherein the direction of higher intensity emissions in the angular emission profile change with the transverse mode structure.

11. The method of claim 7, wherein the semiconductor laser has a ridge width selected to provide transverse mode structures that are different when energized in at least two different ranges of current in order to provide the shift in transverse mode structure.

12. The system of claim 11, wherein the ridge width is between about 1 and 2 wavelengths of the light emitted by the semiconductor laser.

* * * * *